(12) United States Patent
Howe

(10) Patent No.: US 7,914,538 B2
(45) Date of Patent: Mar. 29, 2011

(54) SUTURE ANCHOR INSERTER

(75) Inventor: Jonathan Howe, Mansfield, MA (US)

(73) Assignee: DePuy Mitek, Inc., Raynham, MA (US)

( * ) Notice: Subject to any disclaimer, the term of this patent is extended or adjusted under 35 U.S.C. 154(b) by 383 days.

(21) Appl. No.: 10/878,886

(22) Filed: Jun. 28, 2004

(65) Prior Publication Data

US 2005/0288682 A1 Dec. 29, 2005

(51) Int. Cl.
*A61B 17/56* (2006.01)
(52) U.S. Cl. ....... 606/104; 606/300; 606/314; 606/86 R; 606/232
(58) Field of Classification Search .................... 606/72, 606/86
See application file for complete search history.

(56) References Cited

U.S. PATENT DOCUMENTS

| | | | |
|---|---|---|---|
| 4,898,156 A | 2/1990 | Gatturna et al. | |
| 5,002,550 A | 3/1991 | Li et al. | |
| 5,013,316 A | 5/1991 | Goble et al. | |
| 5,207,679 A | 5/1993 | Li et al. | |
| 5,217,486 A * | 6/1993 | Rice et al. | 606/232 |
| 5,258,016 A | 11/1993 | DiPoto et al. | |
| 5,411,506 A | 5/1995 | Goble | |
| 5,411,523 A | 5/1995 | Goble | |
| 5,417,712 A * | 5/1995 | Whittaker et al. | 606/232 |
| 5,505,735 A | 4/1996 | Li | |
| 5,520,696 A | 5/1996 | Wenstrom, Jr. et al. | |
| 5,522,845 A | 6/1996 | Wenstrom, Jr. | |
| 5,527,342 A | 6/1996 | Pietrzak et al. | |
| 5,607,432 A | 3/1997 | Fucci | |
| 5,683,418 A | 11/1997 | Luscombe et al. | |
| 5,968,078 A * | 10/1999 | Grotz | 606/232 |
| 6,041,485 A * | 3/2000 | Pedlick et al. | 29/450 |
| 6,045,573 A | 4/2000 | Wenstrom, Jr. et al. | |
| 6,527,795 B1 | 3/2003 | Lizardi | |
| 6,610,080 B2 | 8/2003 | Morgan | |
| 2002/0120292 A1* | 8/2002 | Morgan | 606/232 |
| 2002/0147463 A1* | 10/2002 | Martinek | 606/232 |
| 2004/0254580 A1 | 12/2004 | Boock et al. | |

FOREIGN PATENT DOCUMENTS

| | | |
|---|---|---|
| EP | 0 558 993 A | 9/1993 |
| WO | WO 90/09149 A | 8/1990 |

OTHER PUBLICATIONS

EP Search Report dated Oct. 16, 2007 for EP Appl. No. 05253972.3.

* cited by examiner

*Primary Examiner* — Eduardo C Robert
*Assistant Examiner* — Julianna N Harvey

(57) ABSTRACT

An inserter for inserting a suture anchor into bone. The inserter has external markings that uniquely identify the orientations and the relative longitudinal positions of at least two suture passages through a suture anchor releasably engaged with the inserter. The markings assist a surgeon in determining a preferred placement and orientation of the anchor at an operative site during a surgical procedure.

7 Claims, 6 Drawing Sheets

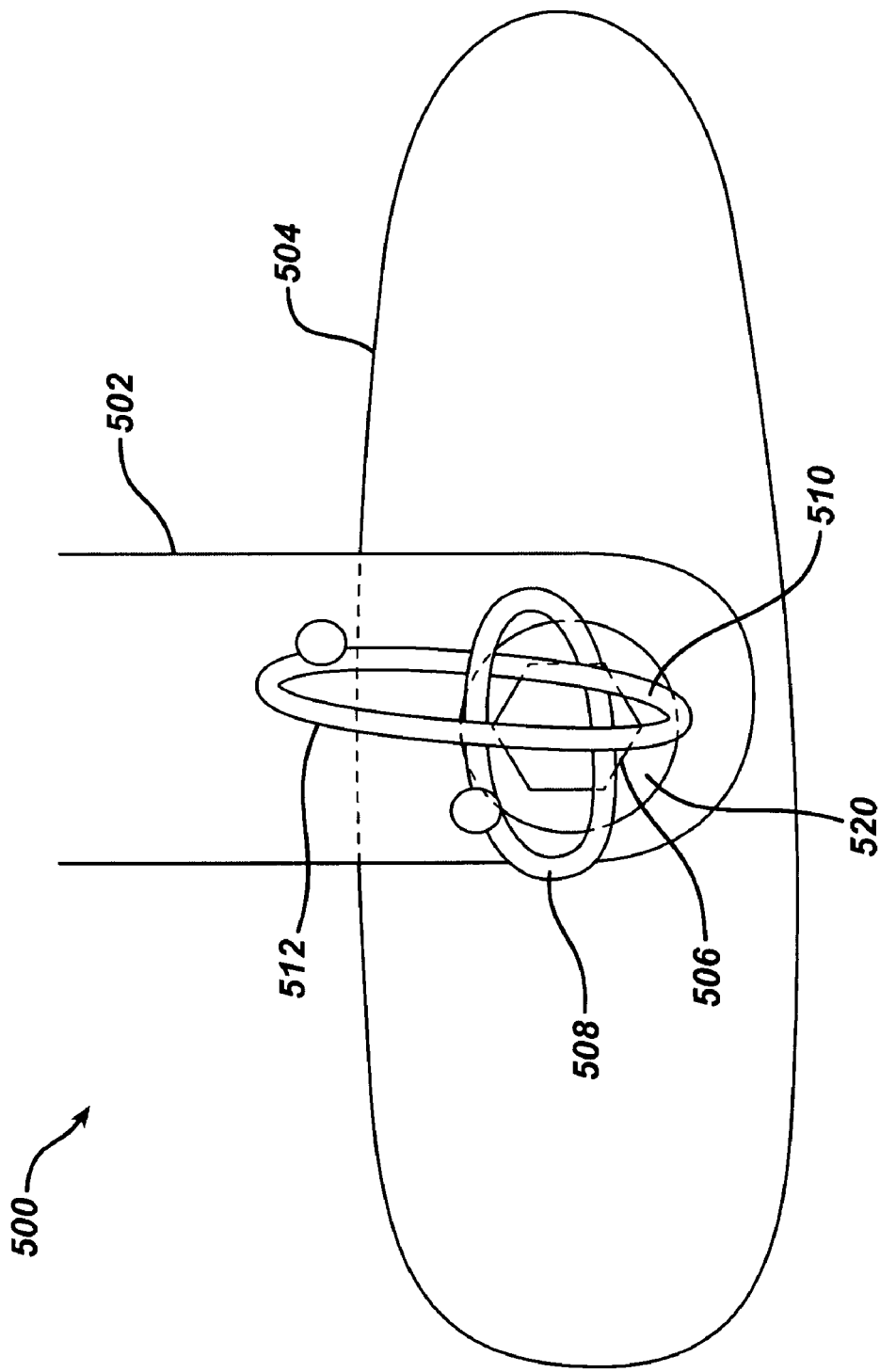

SUTURE ANCHOR INSERTER

FIELD OF THE INVENTION

The field of art to which this invention pertains is soft tissue fixation devices. More particularly, this invention relates to apparatus and methods for inserting suture anchors in bone.

BACKGROUND

Medical devices useful for fixating soft tissue bone are known in the art. These devices include screws, bone pins, staples, sutures and suture anchors. Of particular interest in orthopedic reconstructive surgical procedures, in particular in sports medicine procedures, are suture anchors. Suture anchors typically consist of a member having a suture mounted thereto. Surgical needles are typically mounted to the ends of the suture to provide for the penetration of tissue. A suture anchor is typically inserted into a bore hole drilled into a bone, although the suture anchor may be self-tapping. The suture anchor is secured in the bore hole in a conventional manner by the member, which engages the bone surrounding the bore hole. The suture extends out from the bore hole and is used to attach soft tissue including a tendons, cartilage, ligaments, etc., to the surface of the bone. Most suture anchors typically include some type of a passage, cavity, opening or hole in the member for mounting a suture. The passage may, for example, be a bore extending through the member, a groove or slot in the member, or an eyelet mounted to the member. The passage may be contained in the proximal section of the anchor, the middle, or in a distal section.

Several types of suture anchor devices are known in the art. One type of suture anchor is known as an "arced" anchor. This type of suture anchor is disclosed in U.S. Pat. Nos. 4,898,156, 5,207,679, 5,217,486, 5,417,712, 5,505,735, and 5,522,845, which are incorporated by reference. The arced anchor may have a cylindrical body member. Elastically deformable arc members extend from the body member. Suture is typically mounted in a suture mounting passage in the anchor member or about the anchor member, for example in an eyelet. The arc members are deformed backward during insertion by the hard outer cortex of the bone as the anchor is inserted into a bone bore hole. When in place in the bone bore hole, the arcs subsequently relax in the cancellous bone region, allowing the arcs to engage cancellous bone and thereby fixating the suture anchor in the bore hole.

Another type of suture anchor is a threaded anchor. Many threaded anchors are self-tapping and do not require a pre-drilled bone bore hole, while other threaded anchors require a drilled, or drilled and tapped bore hole. The anchors have an elongated body with a plurality of thread flights, and may include a distal point end. Some threaded anchors include a cutting flute. Threaded anchors typically have a proximal drive end that is engaged by a driving instrument to rotate the threaded anchor into position within the bone. A suture is typically mounted to the anchor, for example, in a hole or passage contained in the anchor body or to an eyelet. Examples of screw threaded suture anchors are contained in U.S. Pat. Nos. 5,013,316, 5,411,506 and 5,411,523, which are incorporated by reference.

Another type of suture anchor that is known in this art is referred to as a "wedge" suture anchor. The wedge anchor typically has a substantially triangular profile, and may have other profiles as well. A suture is typically mounted in a hole or passage contained in the wedge anchor body. The wedge anchor is inserted into a bone bore hole and caused to partially rotate or toggle, thereby causing one or more edges of the anchor to engage bone surrounding the bore hole. Examples of wedge anchors are contained in U.S. Pat. Nos. 5,683,418 and 6,527,795, which are incorporated by reference. Other types of suture anchors are also known in the art including force-fit anchors having compressible and/or expandable anchor bodies, two-piece expansion anchors that are expanded after placement in a bone bore hole, and temperature induced and stress induced shape-memory anchors.

Suture anchors may be designed to accommodate more than one suture mounted to the anchor. These multi-suture anchors are used to achieve satisfactory soft-tissue fixation to a bone surface in certain surgical procedures. For example, multiple sutures mounted to an anchor are often needed in surgical procedures to repair the rotator cuff, in plastic surgery, in cosmetic procedures, and in surgical procedures involving repair of the knee, ankle, elbow, hand, Achilles tendon, etc.

One way to provide multiple suture is to enlarge the passage in the anchor to accommodate multiple sutures. However, there are deficiencies associated with the use of such suture anchors in surgical procedures. The deficiencies include suture binding, tangling, inadvertent knotting and twisting, all of which may interfere with the surgeon's ability to efficiently perform a surgical procedure. Alternatively, an anchor may be designed to accommodate multiple sutures by including multiple passages for sutures. For example, one suture passage through an anchor may be located proximally to another passage through the anchor. Examples of suture anchors having multiple suture passages are contained in U.S. Pat. No. 6,045,573, and copending U.S. patent application Ser. No. 10/458,482, which are incorporated by reference. Anchors having multiple suture passages relieve many of the deficiencies associated with the accommodation of multiple sutures in a single passage.

The correct deployment and positioning of suture anchors and of the sutures mounted thereon, is critical to the success of a surgical procedure. It is therefore important for the surgeon to be able to identify the individual sutures mounted to a multi-suture anchor. Suture identification is typically accomplished by color-coding of the individual sutures mounted to a multi-suture anchor.

When inserting into bone a multi-suture anchor having multiple suture passages, it is often necessary for the surgeon to know which of the multiple sutures is mounted to a particular passage in the anchor. For example, when approximating soft tissue to bone using a multi-suture suture anchor having multiple passages, a surgeon may prefer to first use a suture a suture that passes through a more proximally located suture passage of an anchor, before using a suture that passes through a more distally located suture passage in order to provide optimal soft tissue fixation. Although differentiating sutures by color coding may assist the surgeon, color-coding of sutures alone does not necessarily identify specific locations of suture passages through a multi-suture anchor. In addition, many suture anchor insertion tools hide from the surgeon's view the positions of the suture passages during insertion of the anchor, making it difficult for a surgeon to achieve a desired orientation of the anchor in bone.

Accordingly there is a need in this art for novel suture anchor insertion instruments that can be used with multi-suture anchors that have more than one suture passage, and novel procedures using such instruments, to enable the surgeon to identify individual suture strands with individual suture passages of the anchor.

SUMMARY OF THE INVENTION

Therefore, novel suture anchor inserters are disclosed. A suture anchor inserter of the present invention is particularly useful for deploying a multi-suture anchor in bone, where the anchor has a plurality of suture passages for mounting sutures. A suture anchor inserter of the present invention provides a visual indication to a surgeon of the relative positions of suture passages in the anchor.

An inserter of the present invention includes a hollow elongated member, such as a tubular member having a distal end, a proximal end, an external surface, and a longitudinal axis. The elongated member may be made of stainless steel. The inserter may optionally include a proximal handle that may be cylindrical in shape. The distal end of the shaft is adapted to slidably and releasably engage with a suture anchor, this mating engagement being at a predetermined rotational orientation about the longitudinal axis. Engagement between the inserter and the anchor may be between complementary geometrical shapes. The shapes may be hexagonal, otherwise polygonal, or oval. The shapes may also be keyed to one another. Engagement between the inserter and the anchor is released when the suture anchor is fully inserted into a bone.

The inserter has a first indicator mark aligned with a first suture passage through the anchor, and a second indicator mark aligned with a second suture passage through the anchor. The first suture passage is proximal to the second suture passage along the axis. The first and the second indicator marks uniquely identify the first and the second suture passages, respectively, thereby enabling a surgeon to distinguish between sutures mounted to the anchor at different axial positions. The first and the second indicating mark may be 90 degrees apart radially around the axis, corresponding suture passages that are 90 degrees apart radially on the anchor.

The first and the second indicator marks are visually distinct from one another. To uniquely identify suture passages through the anchor, one of the indicator marks may include a solid line and the other of the indicator marks may include a broken line. The indicator marks may also include text to distinguish between identified suture passages. The marks may be made by a process selected form the group consisting of inkjet printing, chemical etching, laser etching, gas-phase deposition, and electric discharge machining.

Another aspect of the present invention is a suture anchor assembly for deploying a suture anchor in a bone. The assembly includes the above-described inserter. The assembly also includes a suture anchor having at least two suture passages, one distal to the other, and at least one suture mounted in each o suture passage. The suture anchor of the assembly may for example be a threaded anchor, an arced anchor or a toggle-type anchor. The suture anchor is mounted to the inserter.

Yet another aspect of the present invention is a novel method of securing soft tissue to bone using the above described anchor and inserter assembly.

The foregoing and other features and advantages of the present invention will become more apparent from the following description and accompanying drawings.

BRIEF DESCRIPTION OF THE DRAWINGS

FIG. 6 illustrates a suture anchor placed in bone to secure soft tissue to the surface of the bone using an inserter instrument of the present invention.

DETAILED DESCRIPTION OF THE INVENTION

Figure 1:
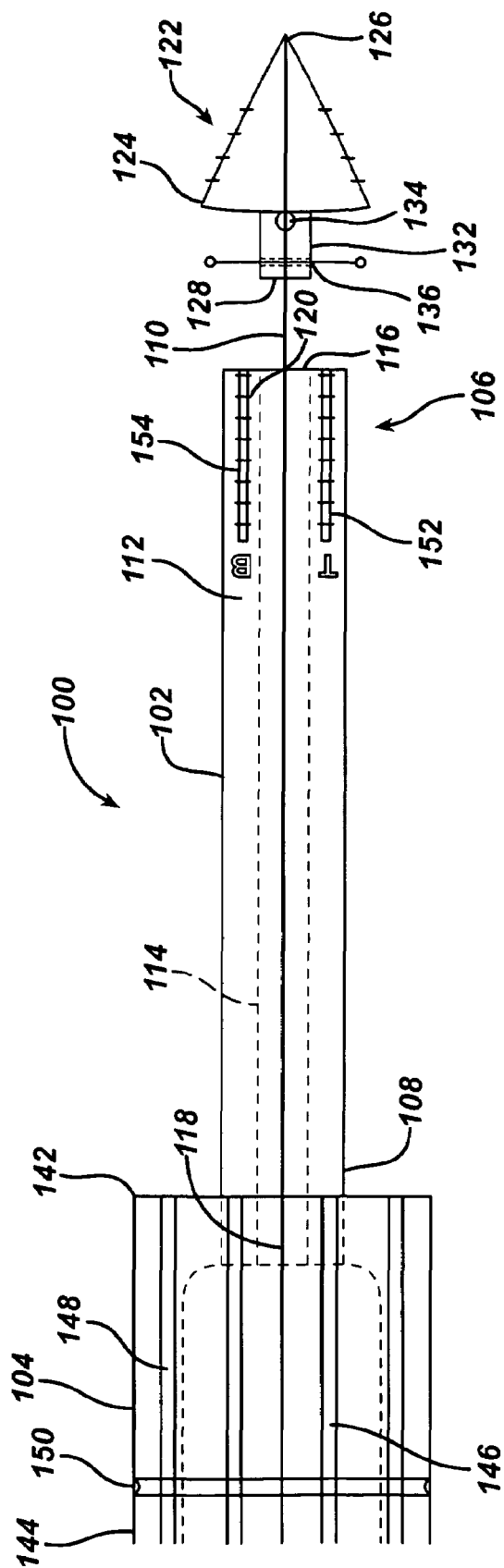
FIG. 1 illustrates a side view of a suture anchor inserter instrument of the present invention, positioned near a suture anchor.

A suture anchor inserter 100 of the present invention is illustrated in FIG. 1. The inserter 100 has a distal tubular member 102 and a proximal handle 104. The tubular member 102 has a distal tube end 106, a proximal tube end 108 and a longitudinal inserter axis 110. The tubular member 102 also has an exterior tube surface 112, a longitudinal passage 114 along the inserter axis 110, a distal end opening 116 and proximal end opening 118. Mounted in the distal tube end 106 is an engagement member 120 adapted for mating engagement with a multi-suture anchor 122. The tubular member may have a variety of external cross-sections including circular, triangular, polygonal, etc. The term "multi-suture anchor" as used herein is defined to mean a suture anchor having at least two separate suture mounting openings, holes, cavities or passages with a suture mounted in each opening, hole, cavity or passage.

The multi-suture anchor 122 is seen to have an anchor body 124 with a distal anchor end 126, a proximal anchor end 128 and an outer anchor surface 130. At the proximal anchor end 128, the anchor 122 includes a drive member 132 adapted for mating engagement with the engagement member 120 of the inserter 100 at a predetermined rotational orientation of the inserter 100 about the inserter axis. A first suture passage 134 having a first suture-passing axis 136 extends through the anchor body 124. A second suture passage 138 having a second suture-passing axis 140 extends through the anchor body 124 proximally to the first suture passage 134. Each of the first 134 and the second suture passage 138 is adapted to receive at least one strand of suture therethrough.

In a preferred embodiment, each of the first and the second suture passages 134 and 138, respectively, is a hole or passage bored through the anchor body 124. In an alternate embodiment, at least one of the first 134 and the second suture passage 138 is a slot in the anchor body 124. The first and the second suture passages 134 and 138 may extend through the drive member 132 or through another portion of the anchor body 124. Preferably, the first suture-passing axis 136 and the second suture-passing axis 140 are substantially transverse to the inserter axis 110. Alternatively, the second suture-passing axis 140 may be angulated with respect to the first suture-passing axis 136, or, the second suture-passing axis 140 may be perpendicular to the first suture-passing axis 136.

The engagement member 120 of the inserter 100 has the form of a socket having a cavity with an internal cross-sectional shape adapted to slidably and releasably engage with a complementary external cross-sectional shape of the drive member 132 of the anchor 122. The engagement between the inserter 100 and the anchor 122 is described as a mating engagement, and a suture anchor engaged with an inserter of the present invention is matingly engaged. The internal cross-sectional shape and the complementary external cross-sectional shape may be any shapes or cross-sections that matingly engage only at specific rotational orientations of the inserter 100 about the inserter axis 110.

In a preferred embodiment, the internal cross-sectional shape and the complementary external cross-sectional shape are substantially hexagonal. Alternatively, the cross-sections may have a variety of geometric configurations including polygonal shape, triangular, arcuate, oval, combinations thereof and the like. Optionally, the internal cross-sectional shape and the complementary cross-sectional shape are mechanically keyed to one another so that the inserter 100 and the anchor 122 matingly engage at only a single rotational orientation of the inserter 100 about the inserter axis 110.

The outer anchor surface 130 is adapted for anchoring the suture anchor 122 in bone. An inserter of the present invention may be used with a suture anchor having any conventional type of bone-anchoring features, and equivalents thereof, sufficient to effectively anchor or maintain the suture anchor in the bone surrounding a bone bore hole. In one embodiment the suture anchor 122 is adapted to include flights of bone-engaging screw threads on the outer anchor surface 130 (a threaded suture anchor). In this embodiment, rotation of the proximal handle 104 about the inserter axis 110 engages the suture anchor 122 with bone. In another embodiment the suture anchor 122 is adapted to include elastic metal tines or "arced" members that protrude from the outer anchor surface 130 for anchoring the suture anchor in bone (a tined or arced suture anchor). In yet another embodiment the suture anchor 122 has a configuration such that it is toggled after insertion into bone to anchor it in place (wedge anchor). In still another embodiment the suture anchor 122 expands to an interference fit after insertion in a bone hole (expansion anchor).

The handle 104 of the inserter 100 is seen to be substantially cylindrically-shaped has a distal handle end 142, proximal handle end 144 and a handle passage 146 communicating between the distal handle end 142 and the proximal handle end 144. The proximal tube end 108 is fixedly mounted to the distal handle end 142 such that the handle passage 146 is in communication with the longitudinal passage 114. The handle 104 is seen to have optional exterior ribs 148, and an optional annular groove 150 located toward the proximal handle end 144. The handle 104 may have other shapes as well including a T-shape. L-Shape, triangular cross-section, polygonal cross-section, etc.

The tubular member 102 may be constructed from conventional biocompatible materials for surgical instruments, having structural strength adequate to engage the suture anchor 122 and drive it into bone. Examples of such construction materials for the tubular member 102 include stainless steel, nickel-titanium alloy, titanium, ceramic, and the like and equivalents thereof. The tubular member 102 may have a circular exterior cross-sectional shape. Alternatively, the tubular member 102 may have a polygonal cross-sectional shape, elliptical, or other geometric cross-section. The handle 104 may be constructed from the same material as the tubular member 102, or from another biocompatible material that may be a structural polymer such as polyethylene, polypropylene, polycarbonate, a polyester and the like and combinations and equivalents thereof.

The tubular member 102 is seen to have a first indicator mark 152 and a second indicator mark 154 on the exterior tube surface 112. When the inserter 100 is in mating engagement with the anchor 122, the first indicator mark 152 is substantially aligned with the first suture passage 134 and the second indicator mark 154 is substantially aligned with the second suture passage 138. That is, a longitudinal extension of the first indicator mark 152 substantially intersects the first suture-passing longitudinal axis 136, and a longitudinal extension of the second indicator mark 154 substantially intersects the second suture-passing longitudinal axis 140.

The first indicator mark 152 uniquely identifies the first suture passage 134 as being distal to the second suture passage 138, and the second indicator mark 154 uniquely identifies the second suture passage 138 as being proximal to the first suture passage 134, for example by marking with the letters "B" and "T", respectively.

Figure 2:
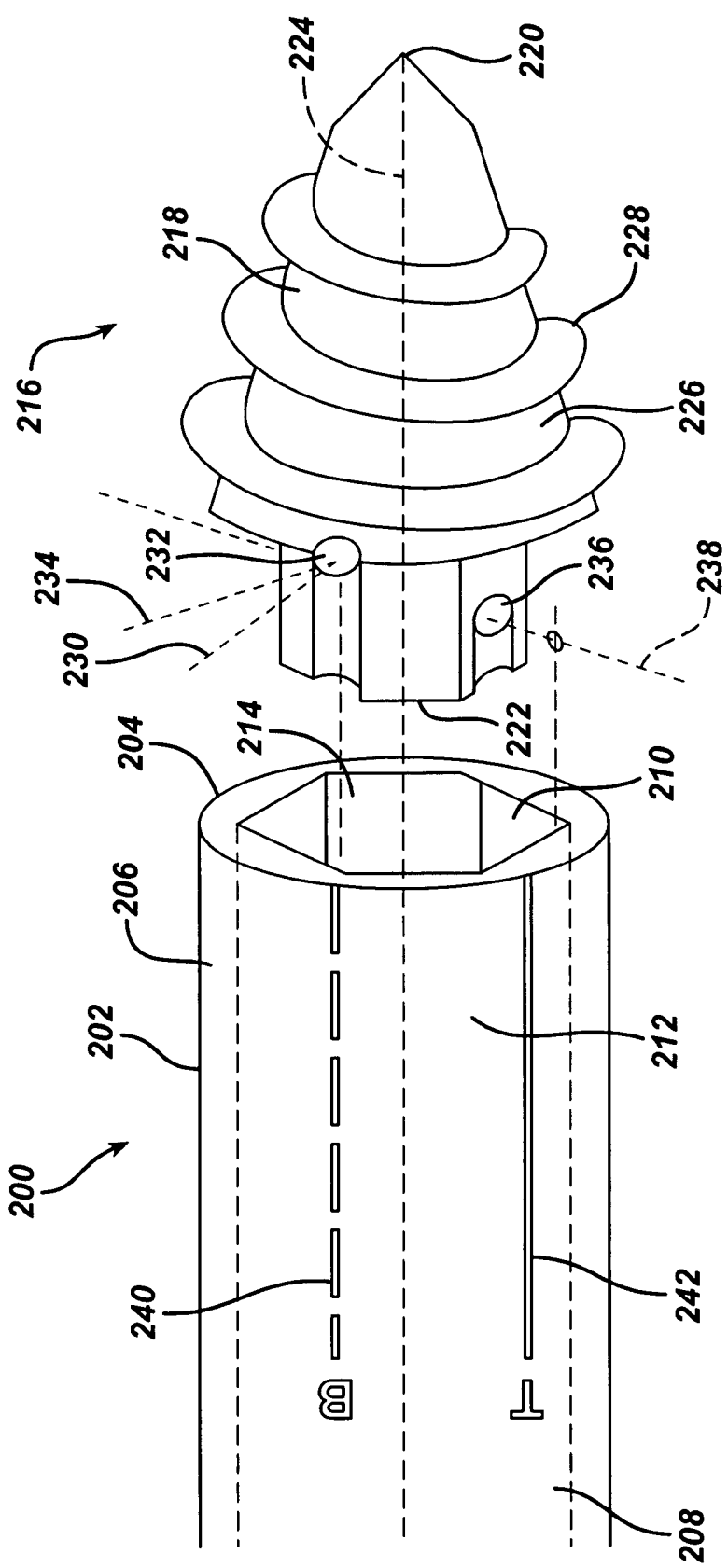
FIG. 2 is a partial perspective view of the distal end of a suture anchor inserter of the present invention, aligned with a suture anchor.

FIG. 2 illustrates a distal portion of an inserter 200 of the present invention. The inserter 200 includes a distal tubular member 202 having a distal tube end 204 and an exterior tube surface 206. The tubular member 202 also has a longitudinal passage 208, a distal end opening 210 and a longitudinal inserter axis 212. The inserter 200 also includes a proximal handle (not shown) as described for the inserter 100 of FIG. 1. Mounted in the distal end 204 of the tubular member 202 is an engagement member 214 having a hexagonal interior cross-section.

The multi-suture anchor 216 has an anchor body 218 having a distal anchor end 220, a proximal anchor end 222, a longitudinal anchor axis 224 aligned with the inserter axis 212, and an outer anchor surface 226 with flights of bone-engaging threads 228 thereon. At the proximal anchor end 222, the anchor 216 includes a substantially hexagonal cross-section drive member 230 adapted for mating engagement with the engagement member 214 at a predetermined rotational orientation of the inserter 100 about the inserter axis.

A first suture passage 232 having a first suture-passing axis 234 extends through the anchor body 218 substantially transversely to the anchor axis 224. A second suture passage 236 having a second suture-passing axis 238 extends through the anchor body 218 proximally to the first suture passage 232 and substantially transversely to the anchor axis 224. The second suture-passing axis 238 is angulated with respect to the first suture passage 234. In a preferred embodiment, the second suture-passing axis 238 is perpendicular to the first suture-passing axis 234, in addition to being proximal to the first suture-passing axis 232. Each of the first 232 and the second suture passage 236 is adapted to receive at least one strand of suture therethrough.

The tubular member 202 is seen to have a first indicator mark 240 and a second indicator mark 242 on the exterior tube surface 206. The second indicator mark 242 is visually distinct from the first indicator mark 240. When the inserter 200 is in mating engagement with the anchor 216, the first indicator mark 240 is substantially aligned with the first suture passage 232 and the second indicator mark 242 is substantially aligned with the second suture passage 236. That is, a longitudinal extension of the first indicator mark 240 substantially intersects the first suture-passing axis 234, and a longitudinal extension of the second indicator mark 242 substantially intersects the second suture-passing axis 238. FIG. 2 illustrates the inserter 200 substantially aligned for mating engagement with the proximal end 222 of suture anchor 216.

The visual distinction between the first and second indicator marks 240 and 242 uniquely identifies the relative axial positions of the first 232 and the second suture passage 236. That is, the first indicator mark 240 uniquely identifies the first suture passage 232 as being distal to the second suture passage 236, and the second indicator mark 242 uniquely identifies the second suture passage 236 as being proximal to the first suture passage 232, this is done in part by the markings "T" and "B". Other markings indicative of distance or relative location may also be used as described herein.

The visual distinction between the first 240 and the second indicating mark 242 can be any distinction that is readily visible to a surgeon using the inserter. For example, indicator marks can be made distinct by line type such as a broken line versus a solid line, or by incorporating textual identifications. Similarly, line length width or color could be used to distinguish between indicator marks. In the embodiment illustrated in FIG. 2, the first indicator mark 40 is a broken line accompanied by an upper case letter "B," identifying the first suture passage 232 as being distal to the second suture passage 236. The second indicator mark 242 is a broken line accompanied by an upper case letter "T," identifying the second suture passage 236 as being proximal to the first suture passage 232.

Indicator marks on an inserter of this invention may be produced using any means that provides visibility of the resulting mark for the surgeon while preserving the structure and biocompatibility of the inserter. Examples of applicable methods for marking an inserter of this invention include printing, etching, anodization, machining, electric discharge machining (EDM), attaching, and laser marking.

Although not shown in FIG. 2, a first diametrically opposed indicator mark may optionally be provided at a position on the exterior tube surface 206 diametrically opposed to the position of the first indicating mark 240. That is, the first indicator mark 240 and the first diametrically opposed indicator mark are separated by 180 degrees about the inserter axis 212. The first diametrically opposed indicator mark may be identical to the first indicator mark, or it may be a unique mark. A second diametrically opposed indicator mark (not shown in FIG. 2) may be optionally provided at a position on the surface 206 of the tubular member 200 diametrically opposed to the position of the second indicator mark 226. That is, the second indicator mark 226 and the second diametrically opposed indicator mark are separated by 180 degrees around the axis 212. The second diametrically opposed indicator mark may be identical to the first indicator mark, or it may be a unique mark.

Figure 3:
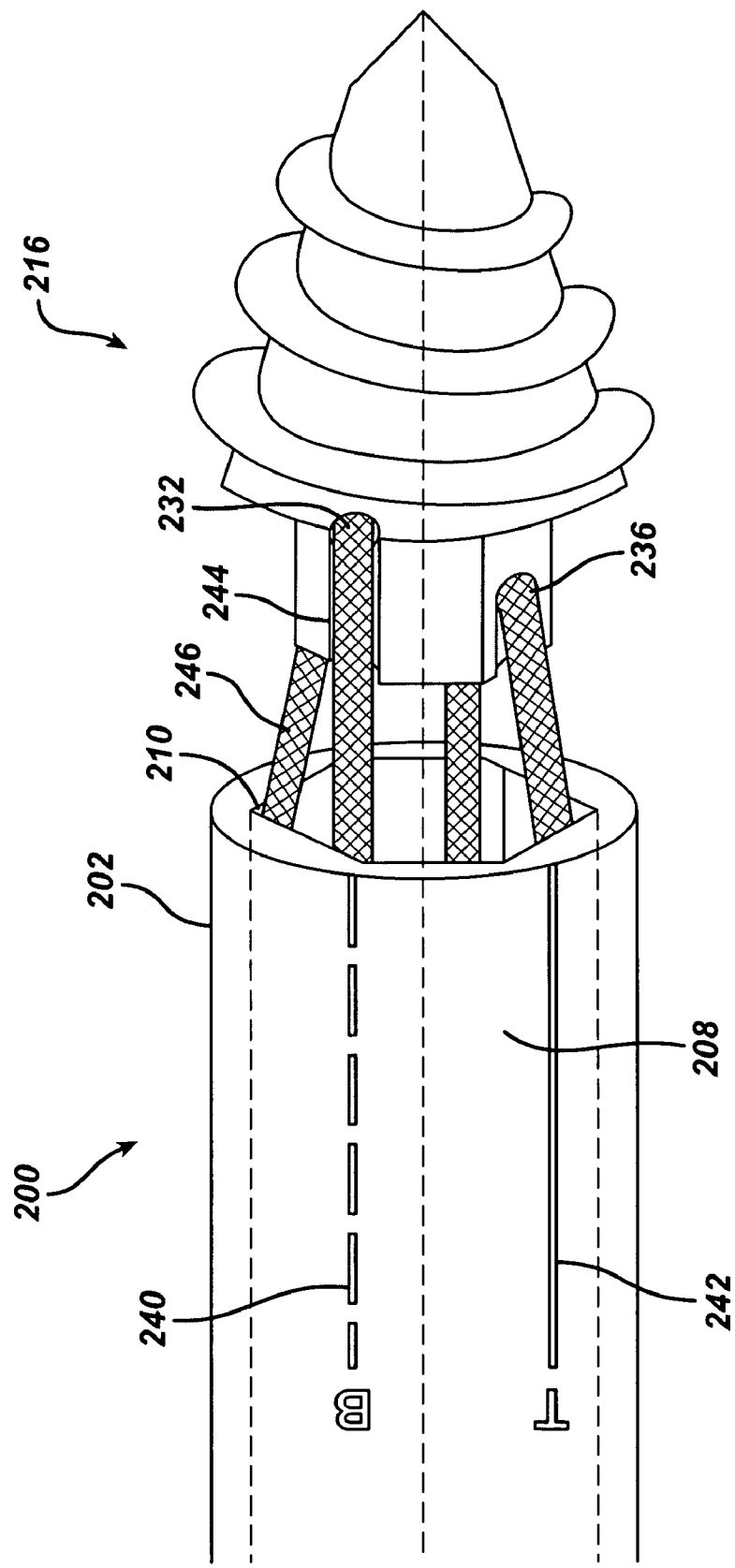
FIG. 3 illustrates the suture anchor inserter of FIG. 2, aligned with a suture anchor with sutures mounted to the anchor prior to mounting the anchor to the distal end of the inserter.

FIG. 3 illustrates the inserter 200 of FIG. 2 with a first suture 244 mounted in the first suture passage 232 and a second suture 246 mounted in the second suture passage 236 (preferably, the sutures are slidable within the passages). The first suture 244 and second suture 246 pass through the first suture passage 232 and the second suture passage 236, respectively; through the distal opening 210 of the tubular member 202, and through the longitudinal passage 208. The tubular member 202 may completely hide the first suture 244 and the second suture 246 from view when the inserter 200 is in mating engagement with the anchor 216, or if desired, windows or slots may be formed in member 202 to provide the surgeon with a view of the sutures while in the tubular member passage 208. Although not preferred, the sutures may be directed outside of the tubular member 202, or through grooves located in the exterior of tube 202.

A suture anchor inserter of the present invention may have as many unique indicator marks as there are suture passages through a matingly engaged suture anchor. For example, a suture anchor inserter of the present invention may be adapted for engagement with a suture anchor having suture passages at three axial positions: distal, central, and proximal. In this example, the suture anchor inserter has three unique indicator marks, one to identify the distal passage, a second to identify the central passage and a third to identify the proximal passage through the anchor.

Figure 4:
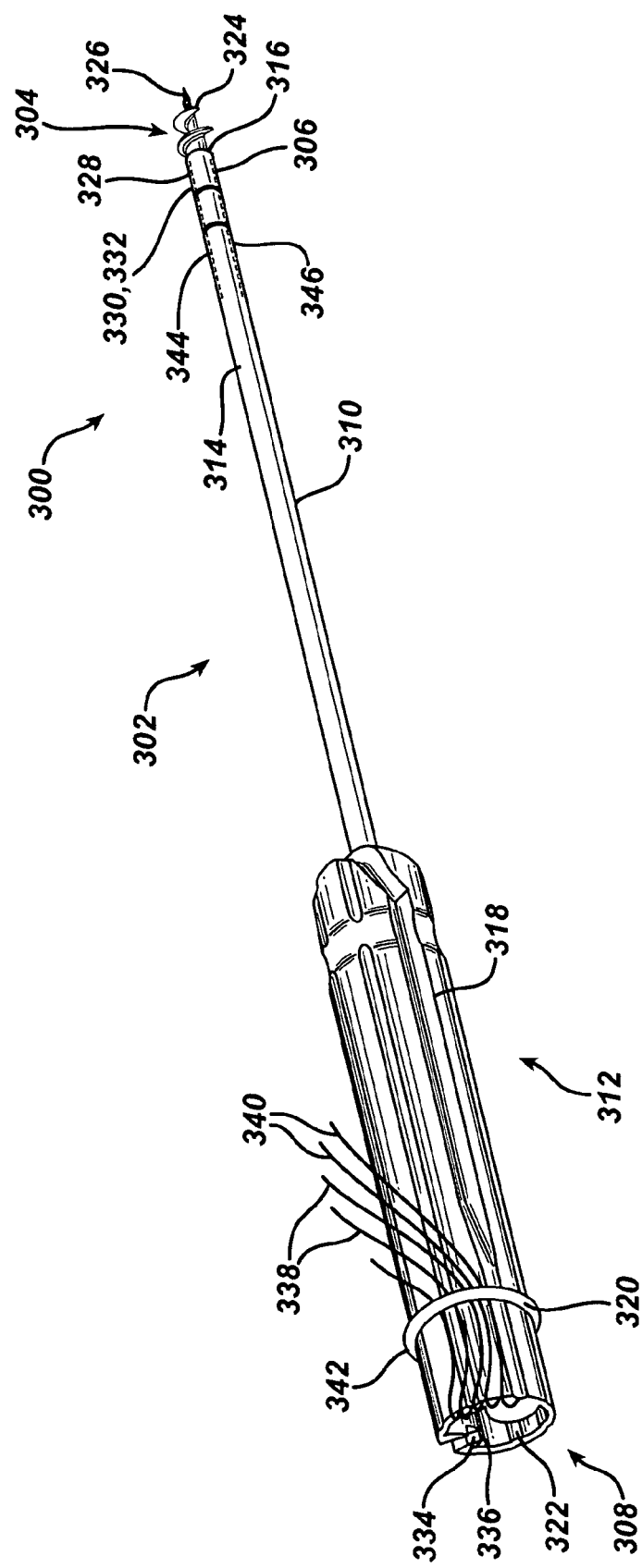
FIG. 4 is a perspective view of an inserter instrument and suture anchor assembly of the present invention.

An inserter of the present invention may be disposable. An inserter of the present invention may be provided as part of a suture anchor assembly that also includes a multi-suture anchor preloaded with sutures for a surgical procedure. Referring to FIG. 4, a suture anchor assembly 300 of the present invention is seen, including a suture anchor inserter 302 and a multi-suture anchor 304. The inserter has a distal inserter end 306 and a proximal inserter end 308. At the distal inserter end 306 is a tubular member 310 extending toward the proximal inserter end 308 and fixedly attached to a proximal handle 312. The tubular member 310 has an outer tube surface 314 and an internal engagement member 316 at the distal end 306 for matingly engaging the suture anchor 304. The handle 312 has an outer handle surface 318 including an annular groove 320. A longitudinal passage 322 extends entirely through the tubular member 310 and the handle 312 between the distal inserter end 306 and the proximal inserter end 308.

The suture anchor 304 has an anchor body 324 having a distal bone-engaging section 326 and a proximal drive end 328 matingly engaged with the inserter 302 at the distal inserter end 306. The drive end 328 is contained within the distal inserter end 306. The anchor 304 also includes a first suture passage 330 through the anchor body 324 and a second suture passage 332 through the anchor body 324. A first suture 334 is mounted to the anchor 304 through the first suture passage 330 and a second suture 336 is mounted to the suture anchor 304 through the second suture passage 332. The first 334 and the second suture 336 pass entirely through the longitudinal passage 322 from the distal inserter end 306 to the proximal inserter end 308 and extend out through the proximal inserter end. Respective ends 338, 340 of the sutures 334, 336 are folded back onto the outer handle surface 318 and an elastic retention ring 342 is rolled over the sutures 334, 336 and contained within the annular groove 320, thereby maintaining the sutures in place.

A first indicator mark 344 on the outer tube surface 314 uniquely identifies the first suture passage 330, and a second indicator mark 346 on the outer tube surface 314 uniquely identifies the second suture passage 332. In a preferred embodiment, the first suture 334 and the second suture 336 are color coded. That is, the second suture 336 is visually distinct from the first suture 334. Color coding of sutures attached to a multi-suture anchor assists a surgeon in identifying individual suture strands among a plurality of suture strands during a surgical procedure, especially when viewing the procedure remotely in an arthroscopic procedure. In another embodiment, one of the first suture 334 and the second suture 336 includes a visible stripe. The assembly 300 may be delivered to a surgeon preassembled with the anchor 304 matingly engaged with the inserter, or may be assembled by the surgeon in the field.

The suture anchors used in a suture anchor assembly of the present invention may be constructed from conventional implantable bio-compatible materials. The materials may be non-absorbable materials such as surgical stainless steel, nickel-titanium alloy, titanium, gold, ceramic, and the like and equivalents thereof. The suture anchors may also be manufactured from conventional bioabsorbable and bioresorbable, bio-compatible polymeric materials including polylactones, polylactides, polyesters, polygalactides, polydioxanone, polycaprolactone, copolymers and blends thereof, hydroxyapatite, ceramics, and the like, and combinations thereof and equivalents thereof.

The sutures that are mounted to the suture anchors used in the combinations of the present invention are formed from conventional polymeric materials and may be absorbable or non-absorbable. Examples of non-absorbable materials include silk, polyethylene, polypropylene, polyvinylidene fluoride, polyesters and the like. Examples of absorbable suture materials include cat gut (collagen), aliphatic polyesters, lactide, glycolide, trimethylene carbonate, polycaprolactone, polydioxanone, and copolymers and blends thereof and the like. The sutures used with anchors in an assembly of the present invention may also be color coded for visibility by a surgeon. For example, one of a first and a second, suture mounted to a suture anchor having two suture passages may include a colored stripe, while the other of the first and the second suture is solid-colored.

Figure 5A:
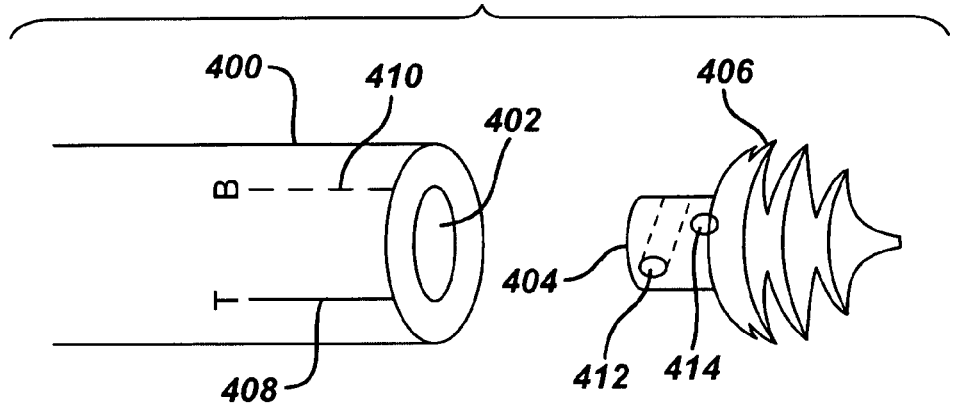
FIGS. 5A-C illustrate examples of various engagement cross-section and types of suture anchors that may be used with the inserter instruments and assemblies present invention.
Figure 5B:
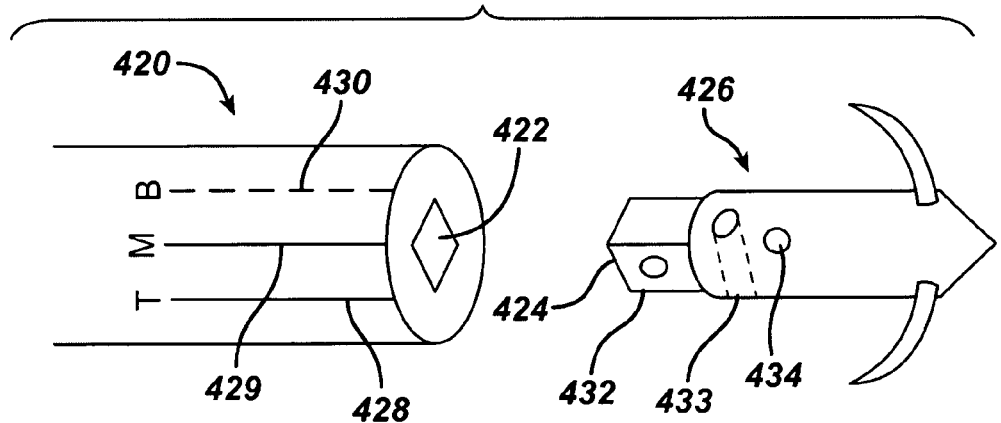
Figure 5C:
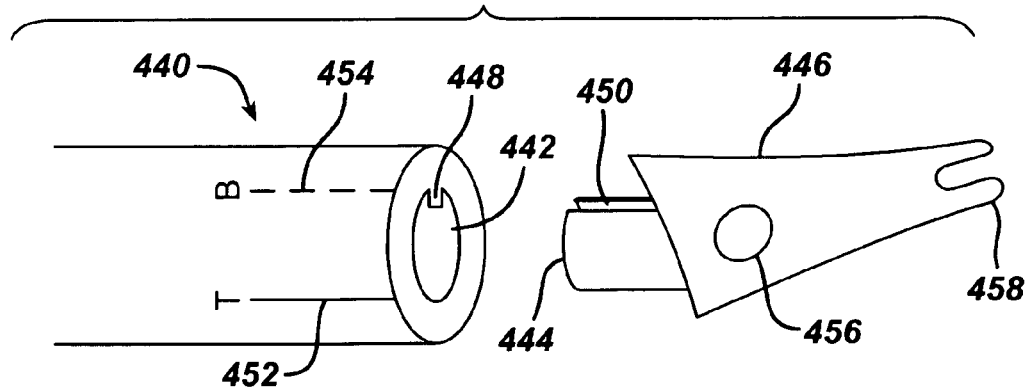

FIGS. 5A, 5B and 5C illustrate examples of the applicability of inserters of the present invention for inserting a variety of types of suture anchors, as well as the capability to engage inserters with various suture anchors using a variety of engagement geometries. FIG. 5A illustrates an inserter 400 of the present invention having an internal oval cross-section engagement member 402 for engagement with an external oval cross-section driver member 404 on a threaded multi-suture anchor 406. The inserter 400 has two unique indicating marks 408, 410 for uniquely identifying each of two suture passages 412, 414 in the anchor 406.

FIG. 5B illustrates an inserter 420 of the present invention having a quadrilateral internal cross-section engagement member 422 for engagement with a quadrilateral cross-section driver member 424 on a tined multi-suture anchor 426. In an embodiment the quadrilateral cross-section is a square. The inserter 420 has three unique indicating marks 428, 429, 430 for uniquely identifying each of three suture passages 432, 433,434 in the anchor 426.

FIG. 5C illustrates an inserter 440 of the present invention having a keyed internal cross-section engagement member 442 for engagement with a complementarily keyed driver member 444 on a wedge-type multi-suture anchor 446. Each of the internal cross-section and the external cross-section are circular and are keyed by a longitudinal rib 448 and groove 450, respectively. The inserter 440 has two unique indicating marks 452, 454 for uniquely identifying each of two suture passages 456, 458 in the anchor 446.

FIGS. 5A, 5B and 5C are meant only to be representative of the applicability of the present invention and are by no means complete with regard to the anchor type, the engagement geometry, or the number of suture passages through an anchor and the corresponding number of unique identifying marks on an inserter. For example, those skilled in the art will appreciate that any of the engagement geometries shown in FIGS. 5A, 5B and 5C may be adapted to be used with any of the anchor types shown. Further, engagement between an inserter and an anchor may be between an external cross-section (i.e., male) of the inserter and an internal cross-section (i.e., female) of a driver member of an anchor.

Among the advantages of suture anchor inserters of the present invention is that they enable a surgeon to position a multi-suture anchor in bone at a preferred orientation to optimize the effectiveness of a surgical procedure, for example, the reattachment of a torn ligament to a bone. An optimally chosen anchor orientation in a bone may provide a more desirable surgical outcome than a randomly chosen anchor orientation. FIG. 6 illustrates a completed soft tissue repair consisting of a surgical reattachment 500 of a tendon 502 to the surface of a bone 504 using a multi-suture anchor 506 that has been inserted into a bore hole 520 in the bone 504 using an inserter of the present invention. In the example of FIG. 6, the multi-suture anchor is oriented so that a more distal passage 506 (deeper in the bone bore hole) carries a first suture 508 positioned for securing transversely to the tendon 502, while a more proximal passage 510 oriented at a right angle to the first passage 506 carries a second suture 512 that is secured more longitudinally in the tendon 502, without binding or other interference between the first suture 508 and the second suture 512.

Although this invention has been shown and described with respect to detailed embodiments thereof, it will be understood by those skilled in the art that various changes in form and detail may be made without departing from the spirit and scope of the claimed invention.

What is claimed is:

1. A suture anchor inserter and suture anchor combination, comprising:
   a suture anchor having an anchor body, a proximal end and a distal end, the suture anchor having a first transverse passage for receiving a suture and a second transverse passage for receiving a suture; and
   a suture anchor inserter having a tubular member having a distal end, a proximal end, an external surface, an internal cross-section, and a longitudinal axis extending between the distal end and the proximal end, wherein the internal cross-section is adapted at the distal end for mating engagement with a suture anchor and the engagement is at a predetermined rotational orientation of the tubular member about the axis, wherein said anchor is mounted to the distal end of the tubular member; and,
   a first distinct indicator mark in or on the external surface of the distal end of the tubular member aligned with the first transverse passage, and a second distinct indicator mark in or on the external surface of the distal end of the tubular member aligned with the second transverse passage, wherein the second transverse passage is proximal to the first transverse passage, wherein the second indicator mark and the first indicator mark are separated by an angle of about 90 degrees radially about the axis, and wherein the second indicator mark uniquely identifies the second transverse passage as being proximal to the first transverse passage; and
   wherein each of the first indicator mark and the second indicator mark comprises at least one character of text.

2. The inserter of claim 1, wherein the tubular member and the anchor are adapted for mating engagement at a single rotational orientation of the inserter about the axis.

3. The inserter of claim 2, wherein the tubular member and the anchor are mechanically keyed to one another.

4. The inserter of claim 1, in which the text of the first indicator mark is indicative of the first transverse passage and in which the text of the second indicator mark is indicative of the second transverse passage.

5. The inserter of claim 4, in which the text the first indicator mark is indicative of a vertical orientation of the first transverse passage with respect to the second transverse passage.

6. A method of attaching soft tissue to the surface of a bone, comprising:
   providing a suture anchor inserter and suture anchor combination, comprising:
   a suture anchor having an anchor body, a proximal end and a distal end, the suture anchor having a first transverse passage for receiving a suture and a second transverse passage for receiving a suture;
   a suture anchor inserter having a tubular member having a distal end, a proximal end, an external surface, an internal cross-section, and a longitudinal axis extending between the distal end and the proximal end, wherein the internal cross-section is adapted at the distal end for mating engagement with a suture anchor and the engagement is at a predetermined rotational orientation of the tubular member about the axis, wherein said suture anchor is mounted to the distal end of the tubular member; and,
   a first distinct indicator mark in or on the external surface of the distal end of the tubular member aligned with the first transverse passage, and a second distinct indicator mark in or on the external surface of the distal end of the tubular member aligned with the second transverse passage, wherein the second transverse passage is proximal to the first transverse passage, wherein the second indicator mark and the first indicator mark are separated by an angle of about 90 degrees radially about the axis, and wherein the second indicator mark uniquely identifies the second transverse passage as being proximal to the first transverse passage and each of the first indicator mark and the second indicator mark comprises at least one character of text;

drilling a bone bore hole in a bone;

inserting the suture anchor into the bore hole such that the anchor is engaged within the bore hole; and, affixing at least a section of soft tissue to the surface of the bone using the sutures.

7. A method of attaching soft tissue to the surface of a bone, comprising:

drilling a bone bore hole in a bone;

manipulating a suture anchor inserter to insert a suture anchor into the bore hole such that the suture anchor is engaged with the bore hole, the suture anchor having a first transverse passage with a suture extending therethrough, and a second transverse passage with a suture extending therethrough, the second transverse passage being proximal to the first transverse passage, and the suture anchor being engaged to a distal end of a tubular member of the suture anchor inserter at a predetermined rotational orientation about an axis of the tubular member, wherein the tubular member includes a first distinct indicator mark in or on an external surface of the distal end of the tubular member aligned with the first transverse passage, and a second distinct indicator mark in or on the external surface of the distal end of the tubular member aligned with the second transverse passage, and wherein the second indicator mark and the first indicator mark are separated by an angle of about 90 degrees radially about the axis, and the second indicator mark uniquely identifies the second transverse passage as being proximal to the first transverse passage and each of the first indicator mark and the second indicator mark comprises at least one character of text; and affixing at least a section of soft tissue to the surface of the bone using the first and second sutures.

* * * * *